(12) United States Patent
Feld

(10) Patent No.: US 11,065,410 B1
(45) Date of Patent: Jul. 20, 2021

(54) DENTAL APPLIANCE USING AIRWAY DIALATION FOR TREATING COVID RELATED BREATHING DISORDERS

(71) Applicant: Leonard Feld, Palm Desert, CA (US)

(72) Inventor: Leonard Feld, Palm Desert, CA (US)

( * ) Notice: Subject to any disclaimer, the term of this patent is extended or adjusted under 35 U.S.C. 154(b) by 0 days.

(21) Appl. No.: 17/164,661

(22) Filed: Feb. 1, 2021

(51) Int. Cl.
*A61M 16/00* (2006.01)
*A61C 9/00* (2006.01)
*A61F 5/56* (2006.01)
*A61M 16/04* (2006.01)
*A61M 16/06* (2006.01)

(52) U.S. Cl.
CPC ......... *A61M 16/0493* (2014.02); *A61F 5/566* (2013.01); *A61M 16/0672* (2014.02); *A61C 9/0006* (2013.01); *A61M 2202/0208* (2013.01)

(58) Field of Classification Search
CPC .. A62B 18/08; A62B 9/06; A62B 9/00; A61F 5/56; A61F 5/566; A61M 16/0493; A61M 16/0672; A61M 2202/0208; A61M 16/0666; A61C 9/0006
See application file for complete search history.

(56) References Cited

U.S. PATENT DOCUMENTS

| 1,873,160 | A | | 8/1932 | Sturtevant | |
|---|---|---|---|---|---|
| 2,470,297 | A | * | 5/1949 | Fields | A61M 15/0098 128/203.15 |
| 3,321,832 | A | * | 5/1967 | Weisberg | A61C 19/045 433/55 |
| 5,513,634 | A | * | 5/1996 | Jackson | A61M 16/0666 128/200.26 |
| 5,537,994 | A | * | 7/1996 | Thornton | A61F 5/566 128/201.18 |
| 5,645,046 | A | | 7/1997 | Kay | |
| 5,752,510 | A | * | 5/1998 | Goldstein | A61M 16/0488 128/200.24 |
| 5,983,892 | A | * | 11/1999 | Thornton | A61F 5/566 128/201.18 |
| 6,012,455 | A | * | 1/2000 | Goldstein | A61M 16/0488 128/204.18 |
| 6,405,729 | B1 | * | 6/2002 | Thornton | A61F 5/566 128/206.29 |
| 6,571,798 | B1 | * | 6/2003 | Thornton | A61M 16/06 128/206.21 |
| 7,676,276 | B2 | | 3/2010 | Karell | |
| 8,333,202 | B2 | | 12/2012 | Lyons | |
| 8,534,278 | B2 | | 9/2013 | Colman et al. | |
| 9,084,863 | B2 | | 7/2015 | Ho et al. | |

(Continued)

FOREIGN PATENT DOCUMENTS

WO WO-0013751 A1 * 3/2000 ........ A61M 16/0666
WO 2006125610 11/2006

*Primary Examiner* — Tu A Vo
(74) *Attorney, Agent, or Firm* — Fulwider Patton LLP

(57) ABSTRACT

A molded breathing appliance for supporting a nasal oxygen tube having an upper bite rim, a lower bite rim, a moldable material disposed within the upper bite rim and lower bite rim for conforming to a patient's maxillary bite impression and mandibular bite impression, respectively, an L-shaped member extending outwardly perpendicular to the upper bite rim, and a transverse support disposed on the L-shaped member and configured with a plurality of sets of oxygen tube finger clamps to retain a nasal oxygen tube in proximity with a patient's nostrils.

12 Claims, 4 Drawing Sheets

(56) References Cited

U.S. PATENT DOCUMENTS

| | | | |
|---|---|---|---|
| 9,610,189 B2 | 4/2017 | Heinonen | |
| 2001/0047805 A1* | 12/2001 | Scarberry | A61M 16/0493 128/206.29 |
| 2004/0003816 A1* | 1/2004 | Cannon | A61M 16/0493 128/207.18 |
| 2005/0022821 A1* | 2/2005 | Jeppesen | A61M 16/0666 128/848 |
| 2006/0207597 A1* | 9/2006 | Wright | A61M 16/0666 128/206.11 |
| 2006/0231101 A1* | 10/2006 | Cannon | A61M 16/0683 128/206.29 |
| 2008/0276938 A1* | 11/2008 | Jeppesen | A61M 16/0493 128/204.18 |
| 2010/0154802 A1* | 6/2010 | Fuselier | A61F 5/566 128/848 |
| 2010/0218773 A1* | 9/2010 | Thornton | A61M 16/0666 128/848 |
| 2010/0224197 A1* | 9/2010 | Keropian | A61M 16/0683 128/848 |
| 2010/0242969 A1* | 9/2010 | Lyons | A61F 5/56 128/848 |
| 2010/0311003 A1* | 12/2010 | Kozlov | A61F 5/566 433/2 |
| 2010/0317987 A1* | 12/2010 | Inoue | A61M 16/125 600/543 |
| 2011/0162658 A1* | 7/2011 | Fisher | A61F 5/566 128/848 |
| 2012/0103343 A1* | 5/2012 | Goldstein | A61M 16/0493 128/207.18 |
| 2012/0255563 A1* | 10/2012 | Thornton | A61C 7/08 128/861 |
| 2013/0130193 A1* | 5/2013 | Fisher | A61C 7/08 433/37 |
| 2019/0240435 A1* | 8/2019 | Anderson | A61M 16/024 |
| 2020/0268999 A1* | 8/2020 | Chang | A61M 16/0683 |

\* cited by examiner

DENTAL APPLIANCE USING AIRWAY DIALATION FOR TREATING COVID RELATED BREATHING DISORDERS

BACKGROUND

This invention relates generally to devices for treating adverse breathing conditions, and more particular to a type of dental apparatus referred to as a dialator that is used with a nasal canula to improve breathing function.

The American Academy of Dental Sleep Medicine (AASDM) recommends oral appliance therapy (OAT) as the first line therapy for the treatment of obstructive sleep apnea (OSA), especially for adult patients that prefer alternative therapies to positive airway pressure (PAP). Other sleep medicine societies including the Brazilian Sleep Odontology Society (ABROS), the World Sleep Society (WSS) and the American Academy of Sleep Medicine (AASM) have also released similar guidelines. OAT devices have important benefits in comparison with PAP devices, including:

1. They do not generate aerosol, which theoretically might increase a chance of infection;
2. They are easy to disinfect, and do not pose a high risk of reinfection; and
3. Their use is associated with higher compliance rates.

PAP therapy also has the potential to expose those who are near OSA patients to an increased risk of COVID-19 in the event the patient is infected.

Thus, there are proven benefits to the use of OAT with both COVID-19 patients and those suffering from OSA. However, what is lacking is a dental appliance/dialator that can secure a nasal cannula in a quick and reliable manner using a patient-custom device that is easy to clean and disinfect.

SUMMARY OF THE INVENTION

The present invention is a breathing appliance that enhances and aides oxygen delivery via a hospital nasal canula respiratory system, particularly during sleep. The appliance is adapted for hospital and medical facilities that use nasal airflow to facilitate and provide increased oxygen to patients with impeded breathing conditions such as obstructive sleep apnea, obstructive sleep hypopnea, upper airway resistance syndrome, and COVID Related Breathing Disorders (CRBD). The appliance comprises a one piece molded malleable bite block having an upper (maxillary) bite rim and a lower (mandibular) bite rim, where the lower bite rim is offset from the upper bite rim by approximately one to two millimeters to reposition the jaw's alignment and open the nasal breathing passage. The upper and lower bite rims are placed in adjacent bite position, and the malleable aspect of the bite block allows for customization of the respective rims to the individual patient's dental impressions. In one example, the bite block is made of, or include, a material that can be heated to soften the material, whereupon the patient bites into the material to form a mold of the patient's teeth and gum configuration. The bite block is then cooled to room temperature where it hardens, establishing a custom bite block suited for the selected patient. This ensures proper alignment in the patient's mouth with little to no slippage, shifting, or discomfort.

A rigid L-shaped support is formed in the appliance and extends outwardly from the upper bite rim, the support comprising a horizontal spacer and a vertical extension at substantially a right angle. The horizontal spacer projects out of the patient's mouth when the appliance is bitten by the patient, and the vertical extension has a length that places the distal end adjacent the patient's nostrils. A transverse oxygen tube clamp is formed at the top of the vertical extension that includes a central support and first and second peripheral supports sized to receive and secure a conventional nasal oxygen tube. Such oxygen tubes are typical placed against the patient's upper lip and secured with a cord or tether that goes around the patient's neck. Here, the clamp holds the tubes adjacent the patient's nasal breathing passage, fixed by the appliance's upper and lower bite rims. Dislodging of the oxygen tube during sleep is resisted by the appliance's fixture to the patient's dental physiology, and breathing can be enhanced by the proper positioning (or repositioning) of the patient's lower jaw to expand the breathing passage.

The appliance of the present invention provides a Mandibular Advancement Repositioning Appliance (MARA) that causes the nasal delivery component to be placed and maintained in a positive alignment regardless of the patient's movements. This is particularly critical during sleep, when the patient's jaw relaxes and can obstruct the breathing pathway. OSA occurs when the tongue and other soft tissue relax during sleep and obstructs the airway. With a diminished supply of fresh air, the patient's oxygen level in the blood decreases. In most patients, this leads to repeated awakenings as the brain detects the reduced oxygen level and arouses the body from sleep temporarily in order to open the airway. Regular breathing is thus restored, but once the patient falls asleep the cycle repeats itself over and over. These repeated awakenings can happen hundreds of times over the course of a night's sleep, preventing the patient from falling into a deep sleep. This in turn can lead to conditions arising from sleep deprivation, such as heart attacks, high blood pressure, stroke, heart failure, arrythmia, extreme fatigue, and weight gain. The present solution is to treat the breathing condition with an intraoral appliance that can serve to open the nasal pharyngeal airway by positioning the jaw in a forward (anterior) position during sleep. The repositioning of the jaw widens the airway and permits increased flow of oxygen through the nasal passage. The present invention is a molded single piece that can be easily sanitized, custom fit, and reused over and over again.

These and other advantages of the invention will best be understood with reference to the accompanying drawings listed below in conjunction with the detailed description of the invention.

DETAILED DESCRIPTION OF THE PREFERRED EMBODIMENTS

Figure 1:
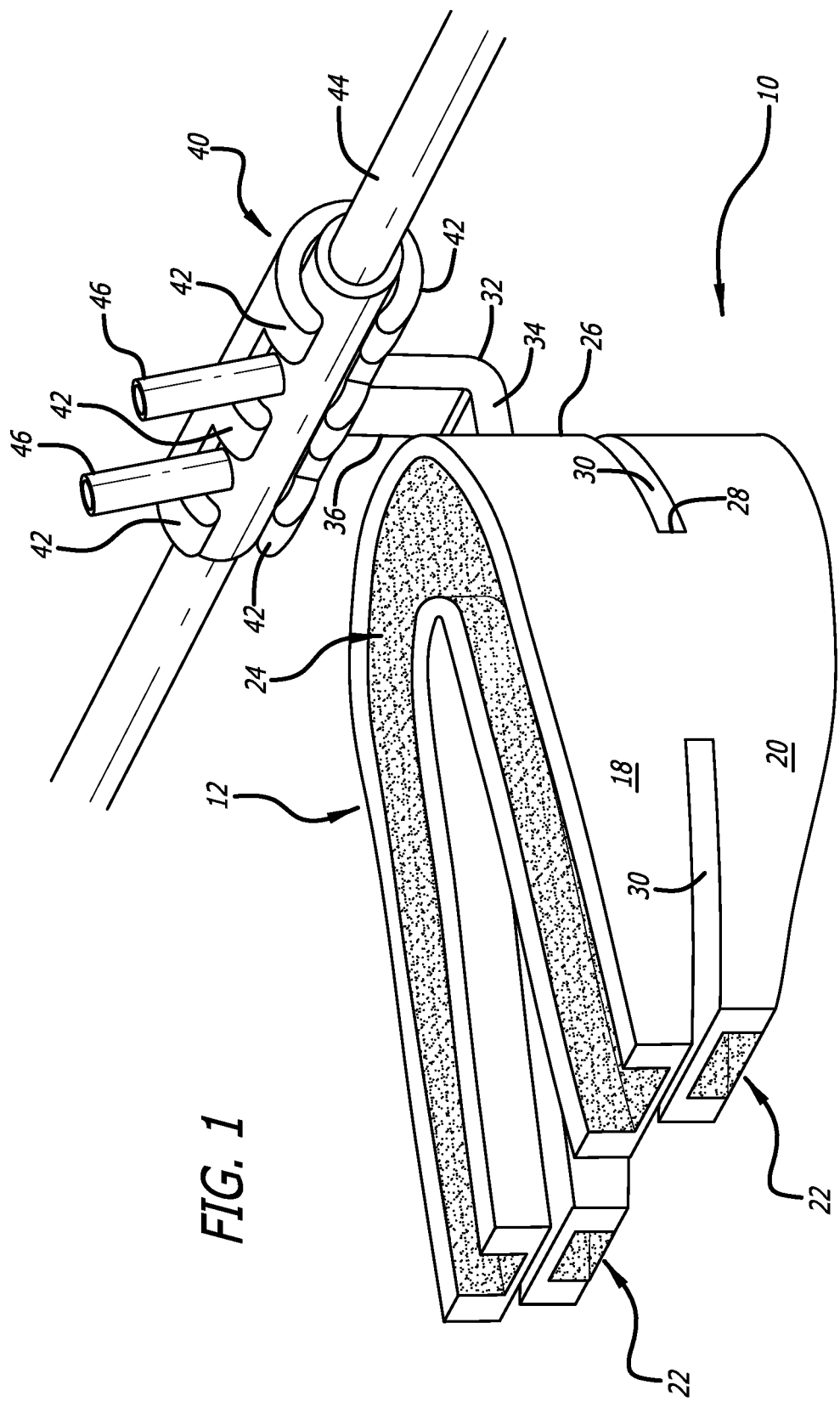
FIG. 1 an elevated, perspective view of a first preferred embodiment of the present invention.
Figure 4:
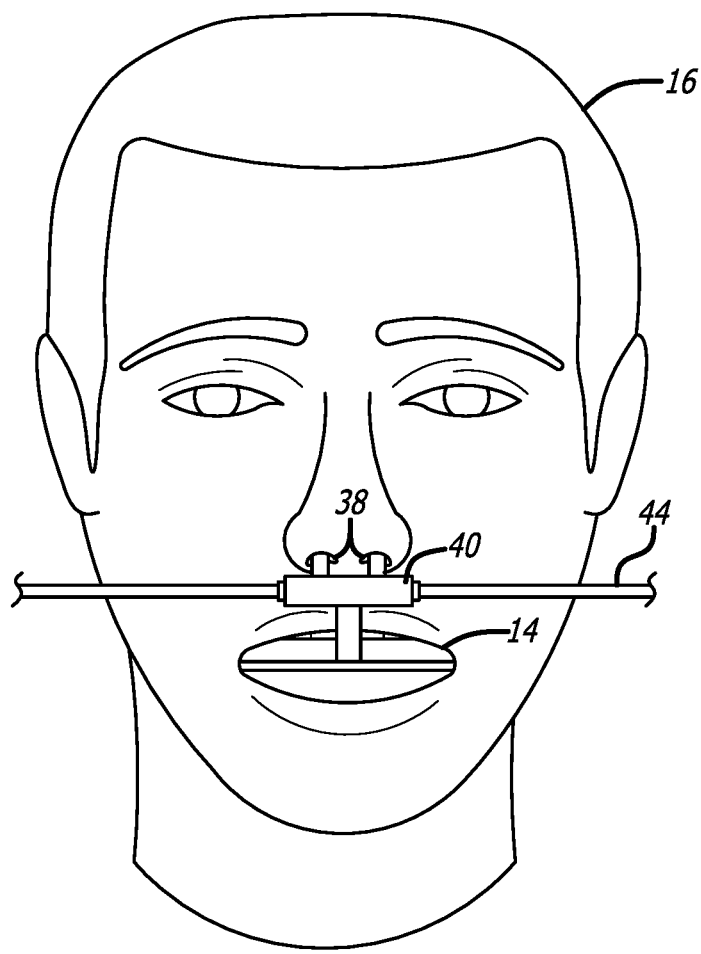
FIG. 4 is a front view of the present invention inserted into a human.

The present invention is generally shown in FIGS. 1 and 4, and comprises a single piece of unitary molded plastic that is adapted to be modified in order to customize the fit of the appliance to a particular patient. The appliance 10 is a U-shaped block 12 sized to fit into the mouth 14 of a patient 16, where the block 12 is formed with upper and lower bite rims 18, 20 defining dental channels 22 that receive the patient's teeth. The block 12 may be constructed of a rigid plastic material that can be molded to form the entire unitary device, and the dental channels 22 can be filled with a casting material 24 that is more malleable in a first state and less malleable in a second state. An example of this is a "boil and bite" material where the appliance is placed in heated water. The water softens the casting material, e.g. ethylene-vinyl acetate ("EVA"), such than when the patient subsequently bites down on the casting material, an impression of the patient's dental pattern is permanently formed in the material. The device cools and preserves the patient's dental fit so that the appliance becomes a custom, personalized appliance that is fitted to a unique dental configuration.

The block 12 preferably includes a smooth peripheral edge 26 and the upper bite rim and lower bite rim are connected by left and right bridges 28. Fore and aft of the bridges, a small gap 30 separates the upper 18 and lower 20 bite rims, but the bridges 28 are sized to provide stability to the appliance 10 to prevent rocking or relative movement of the opposed bite rims when the patient bites down on the appliance. The upper bite rim 18 is configured with a rigid L-shaped support 32 extending from the smooth peripheral outer surface 26 at the forward/center edge. The rigid L-shaped support 32 extends out of the patient's mouth 14 when the patient's teeth are disposed within the dental channels 22, and comprises a horizontal spacer 34 and a vertical extension 36, such as but not limited to a ninety degree arrangement.

The horizontal spacer 34 projects out of the patient's mouth when the appliance is bitten by the patient 16, and the vertical extension 36 has a length that places its top edge adjacent the patient's nostrils 38. Formed at the top edge of the L-shaped support 32 is an oxygen tube clamp 40 adapted to retain a nasal oxygen cannula in proximity with the patient's nostrils. The clamp 40 is formed with tube supports in the form of opposed sets of curved fingers 42 that grip the oxygen tube 44 and maintain the tube in a preferred location and orientation. Each set of curved fingers 42 cooperate to form a semi-cylindrical grip that holds the tube 44 in proximity with the patient's nostrils. In a preferred embodiment, the grips are located at each end of the clamp 40 and a grip at the center of the clamp to secure a nasal oxygen tube. The clamp holds the tube's gas exit ports 46 adjacent the patient's nasal breathing passage, fixed by the appliance's upper and lower bite rims 18, 20. In a preferred embodiment, the grips orient the gas exit ports 46 at an angle of between thirty and sixty degrees (30°-60°), and more preferably to an angle of approximately forty-five degrees (45°) relative to the vertical extension 36 to "aim" the flowing oxygen upward and into the nasal passage. Breathing can be enhanced by the proper positioning (or repositioning) of the patient's lower jaw to expand the breathing passage while the nasal cannula is secured adjacent the patient's breathing passage.

Figure 2:
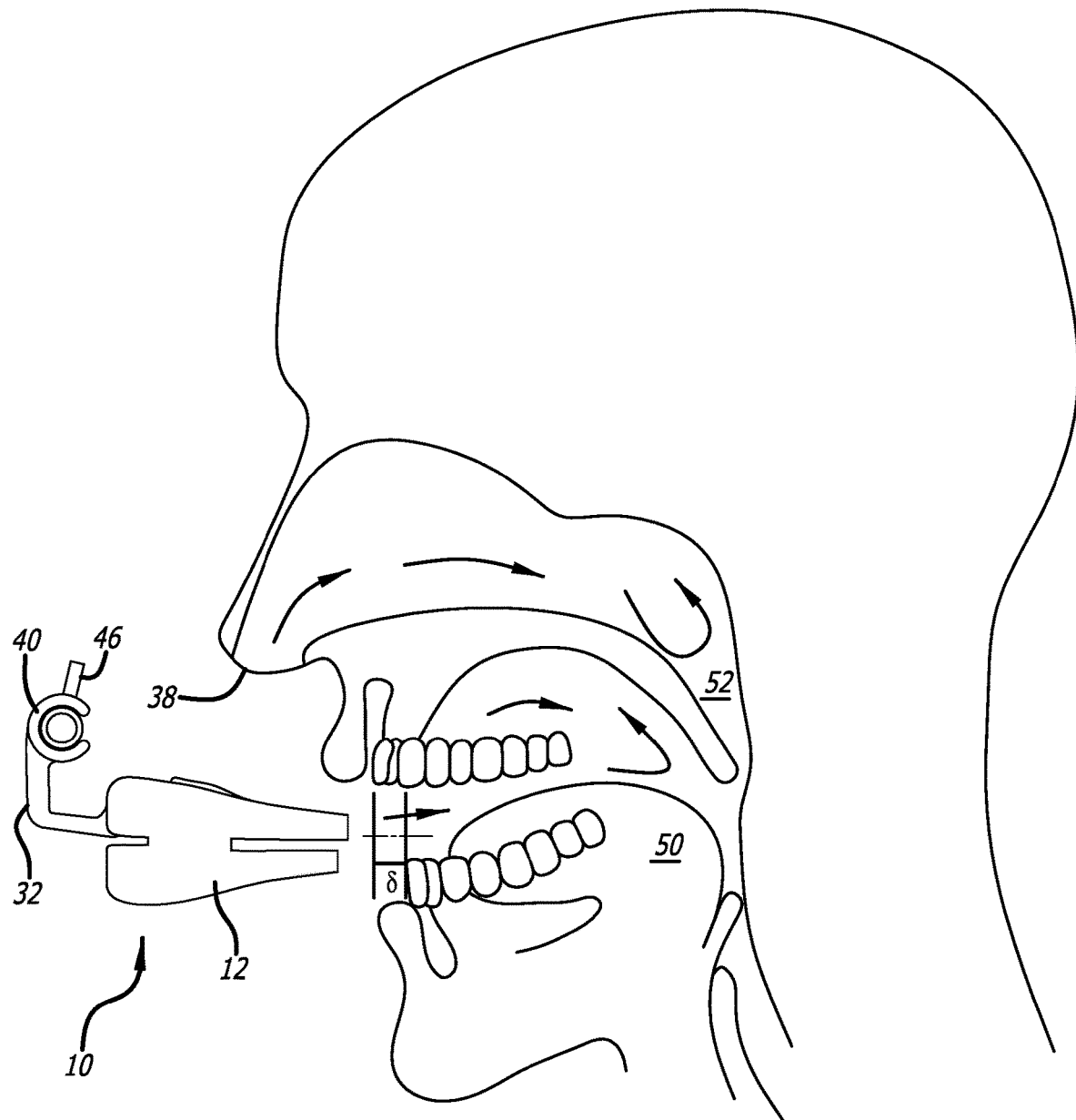
FIG. 2 is a side view of a human breathing path occluded prior to insertion of the present invention.
Figure 3:
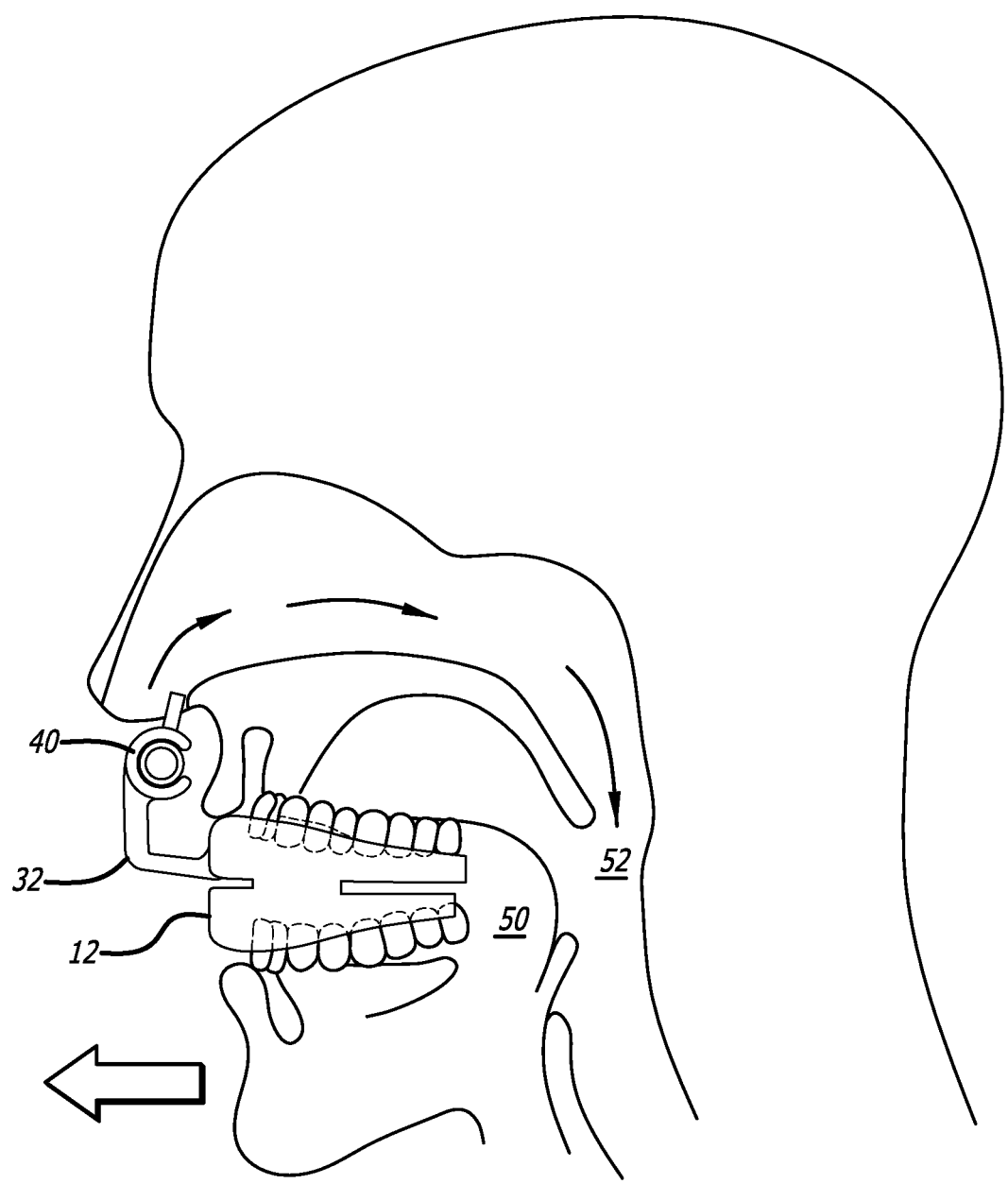
FIG. 3 is a side view of the human breathing path open after insertion of the present invention.

FIGS. 2 and 3 illustrate the manner in which the present invention addresses adverse breathing conditions, particularly when the patient is asleep. In FIG. 2, prior to insertion of the appliance 10, the patient's breathing path is partially occluded as the tongue 50 and other soft tissue relax during sleep and slip into the breathing path 52. The patient suffers from a deprivation of oxygen, causing the patient to either snore to obtain more oxygen or awaken due to the lack of oxygen. In FIG. 3, the appliance 10 has repositioned the patient's jaw anteriorly relative to the upper bite position (as compared with FIG. 2) to open or widen the patient's nasal pharyngeal airway, allowing oxygen from the nasal canula to more freely enter the patient's respiratory system. If one assumes that the nasal pharyngeal airway has a roughly circular profile, then opening the airway by a factor of $\Delta R$ has the effect of increasing airflow by $(\Delta R)^2$, dramatically improving the amount of air that can pass through the airway. In a preferred embodiment, the displacement $\delta$ of the lower bite rim is ~1-2 mm, which increases the airway without making the patient uncomfortable and impairing sleep.

While the foregoing description and depictions illustrate a preferred embodiment, the present invention is not limited to those descriptions and depictions. Rather, one of ordinary skill in the art will readily recognize and appreciate several alternate embodiments falling within the spirit of the present invention. Therefore, unless expressly stated, the scope of the invention is not limited to any specific embodiment or description, but rather defined by the words of the appended claims read consistent with, but not confined by, the foregoing description and drawings.

I claim:

1. A single piece, molded breathing appliance for supporting a nasal oxygen tube, comprising:
    an upper bite rim;
    a lower bite rim;
    an intermediary bridge connecting a portion of a lower surface of the upper bite rim to a portion of an upper surface of the lower bite rim;
    a moldable material disposed within the upper bite rim and lower bite rim, said moldable material adapted to set after conforming to a patient's maxillary bite impression and mandibular bite impression, respectively;
    an L-shaped member projecting outwardly and perpendicular to the upper bite rim, the L-shaped member comprising a flat horizontal spacer and flat vertical extension; and
    a transverse tube clamp disposed on the vertical extension of the L-shaped member, wherein the transverse tube clamp comprises a diameter and a length, such that when the appliance is worn by the patient, the length extends horizontally from a first lateral side to a second lateral side of the patient and wherein the transverse tube is configured with a plurality of sets of opposed semi-cylindrical clamps adapted to cooperate to retain the nasal oxygen tube in proximity with the patient's nostrils.

2. The breathing appliance of claim 1, wherein the plurality of sets of opposed semi-cylindrical clamps orient a flow of oxygen at an angle of between thirty and sixty degrees relative to the vertical extension.

3. The breathing appliance of claim 1, wherein the plurality of sets of opposed semi-cylindrical clamps orient a flow of oxygen at an angle of approximately forty-five degrees relative to the vertical extension.

4. The breathing appliance of claim 1, wherein the moldable material sets after being heated to at least 140° F.

5. The breathing appliance of claim 1, wherein the moldable material includes ethylene-vinyl acetate (EVA).

6. The breathing appliance of claim 1, wherein the lower bite rim is anteriorly offset from the upper bite rim to increase a patient's pharyngeal nasal breathing passage.

7. The breathing appliance of claim 6, wherein the offset is between 1 and 2 mm.

8. A system for delivering oxygen to a patient through a nasal cannula, comprising:
    a supply of oxygen;
    an oxygen tube; and a single piece, molded breathing appliance for supporting the oxygen tube, comprising an upper bite rim, a lower bite rim, an intermediary layer connecting a portion of a lower surface of the upper bite rim to a portion of an upper surface of the lower bite rim, a moldable material disposed within the upper bite rim and lower bite rim, said moldable material adapted to set after conforming to the patient's maxillary bite impression and mandibular bite impression, respectively, an L-shaped member extending outwardly perpendicular to the upper bite rim, the L-shaped member comprising a horizontal spacer and a vertical extension, and a transverse support disposed on the L-shaped member, wherein the transverse support comprises a diameter and a length, such that when the appliance is worn by the patient, the length extends horizontally from a first lateral side to a second lateral side of the patient and wherein the transverse support is configured with a plurality of sets of oxygen tube finger clamps to retain the oxygen tube in proximity with the patient's nostrils.

9. The system of claim 8, wherein the moldable material sets after being heated to at least 140° F.

10. The system of claim 8, wherein the moldable material includes ethylene-vinyl acetate (EVA).

11. The system of claim 8, wherein the lower bite rim is anteriorly offset from the upper bite rim to increase a patient's pharyngeal nasal breathing passage.

12. The system of claim 11, wherein the offset is between 1 and 2 mm.

* * * * *